US00PP08657P

United States Patent [19]

Hill, Jr.

[11] Patent Number: Plant 8,657

[45] Date of Patent: Mar. 22, 1994

[54] VRIESEA PLANT NAMED JUNE

[76] Inventor: Herbert Hill, Jr., 1040 Jameson Rd., Lithia, Fla. 33547

[21] Appl. No.: 444

[22] Filed: Jan. 4, 1993

[51] Int. Cl.[5] ..... A01H 5/00

[52] U.S. Cl. ..... Plt./88.8

[58] Field of Search ..... Plt. 88.8

*Primary Examiner*—James R. Feyrer

*Attorney, Agent, or Firm*—Foley & Lardner

[57] ABSTRACT

A new cultivar of Vriesea plant named June, characterized by its very wide inflorescence relative to the overall size of the plant, abundant medium green foliage in a dense rosette, spectacular scape, arrangement and branches, all bright red in color, heavy floral branching, erect scape and alternately arranged bracts, and yellow flowers associated with each bract.

2 Drawing Sheets

The present invention comprises a new and distinct cultivar of Vriesea plant, referred to by the cultivar name June. The genus Vriesea is of the family Bromeliaceae.

June is a product of a planned breeding program conducted in Lithia, Fla. June was originated by the inventor Herbert Hill, Jr., from a hybridization made in the program in which the female or seed parent was an unnamed cultivar of Vriesea×Brentwood, and the male or pollen parent was a cultivar resulting from the cross of V. Vigeri×V. Cardinalis.

June was discovered and selected within the progeny of the stated parentage by Herbert Hill, Jr. in Spring 1984 in a controlled environment in Lithia, Fla. Subsequent asexual reproduction of June by Herbert Hill, Jr. in Lithia, Fla. by offshoots has demonstrated that the combination of characteristics as herein disclosed for June are firmly fixed and retained through successive generations of asexual reproduction.

June has not been observed under all possible environmental conditions. The phenotype may vary significantly when grown under different conditions of temperature, light, and other determining factors, without, however, any variation in the genotype. The following observations, measurements and comparisons describe plants grown in Lithia, Fla. under greenhouse conditions which closely approximate those generally used in commercial practice.

The following traits have been repeatedly observed and are determined to be basic characteristics of June which in combination distinguish this Vriesea as a new and distinct cultivar:

1. The total inflorescence is very wide in relation to the diameter of the foliage and the height of the plant.
2. Abundant solid medium green foliage in a dense rosette.
3. Spectacular scape arrangement and branches, all bright red in color.
4. The compound inflorescence contains nine or more branches, which are up to 24 cm in length.
5. The floral bracts are carried on an erect scape, are sharply ridged and up to 42 mm in length.

The new cultivar can be compared in certain respects to cultivars of *V. poelmanii*. The respective plant shapes are similar and both have red inflorescence. However, June has many more leaves, with its leaves being longer and narrower; a longer and smaller diameter scape, more branching in its inflorescence, and more remote floral bracts, as opposed to the thicker and umbricate bracts of the comparison cultivars.

In the accompanying color photographic drawings, sheet 1 comprises a perspective view of the inflorescence and foliage characteristics of June. Sheet 2 comprises an enlarged photograph showing the scape, bracts, and flowers in more detail. The colors are as nearly true as possible with illustrations of this type.

In the following description, color references are made to The Royal Horticultural Society Colour Chart, except where color terms of ordinary significance are used. The color values were determined between 10:30 a.m. and 11:30 a.m. on Sep. 10, 1992, under slightly clouded but bright daylight conditions at Lithia, Fla.

Classification:

*Botanical.*—Vriesea cv June.

PLANT

Form: Rosette.

Height: 55 to 65 cm when grown in 13 cm pot, and approximately 60 cm in diameter when fully grown.

Growth habit: Excellent, very vigorous.

Method of propagation: By offshoots, which often exceed 20 in number.

Foliage:

*Quantity.*—Abundant.

*Size of leaf.*—27 to 35 cm in length; width at tip is 0.5 cm and in middle is 3.5 to 4.0 cm.

*Shape of leaf.*—Oblong with tips slightly bending down; rounded and apiculate.

*Surface texture.*—Glabrous.

*Margin.*—Entire.

*Color.*—Upperside 137A; underside 146A color is solid with no patterns or striping.

*Veins.*—Upper surface: Slightly visible Under surface: Visible

*Sheaths.*—Broad, distinct, green, much wider than blades.

INFLORESCENCE

Bracts:

*Scape.*—Erect, 8 mm in diameter; scape bracts erect, imbricate, broadly ovate, apiculate, spreading, 43 mm long, 2 cm wide, light green, red-tinged, with dark green tip. Inflorescence laxly bipinnate, 8–12 spikes, 3–5 cm long; primary bract broadly ovate, apiculate, 45 mm long, 3 cm wide, many times shorter than raceme, cherry red; racemes spread with maturity, lax, 10–14 flowered, naked at base or with a single sterile bract, lanceolate, acute, compressed, 14–21 cm long, 3–6 cm wide; rachis nearly straight, curving noticeably upward at maturity, glabrous, color cherry red 45A-B.

*Floral bracts.*—Distichous, imbricate, becoming lax with rachis exposed at maturity, broadly ovate, broadly acute, sharply carinate and incurved, exceeding the sepals; floral bracts 35–45 mm long, 25–28 mm wide, membranaceous, nerved, glabrous, color cherry red 45A-B.

Flowers: Typical, borne at and extending outwardly of floral bracts, one flower per bract; flowering normally in progression from base to tip of scape or bracts, with many flowers blooming at same time (see photos). Main flower color 17A. Flowers never secund; pedicels very short. Sepals narrowly elliptic, acute, nerved, 35 mm long, 10 mm wide, yellow; petals linear, obtuse, 5 cm long, 6 mm wide, bearing 2 large obtuse scales at base.

Reproductive organs: Stamens and style exserted, stigma and style 52 mm long, anther and filament 55 mm long, ovary 1 cm long, 3 mm wide; capsule slender, acute, approximately 3 cm long; seed fusiform with long straight basel coma.

Duration of blooming: After bud is visible, approximately one month is required for inflorescence to extend and develop. From this point the lateral spikes fold down and away from the scape. With anthesis, the lower flower bracts (calyx) of the terminal spike and lateral spikes being spreading and become lax. Floral bracts continue to spread as flowers develop until entire inflorescence is lax. During the period of flowering, the lateral spikes develop a unique bending. At a point approximately 4 cm from the rachis, the lateral spikes turn noticeably upward producing an angle of 35–45 degrees. Depending on conditions, flowering extends over 1½–2½ months. After flowering, inflorescence color remains for 1–3 months.

Resistance to disease: No disease problems have been noted to date.

I claim:

1. A new and distinct cultivar of Vriesea plant named June, as illustrated and described.

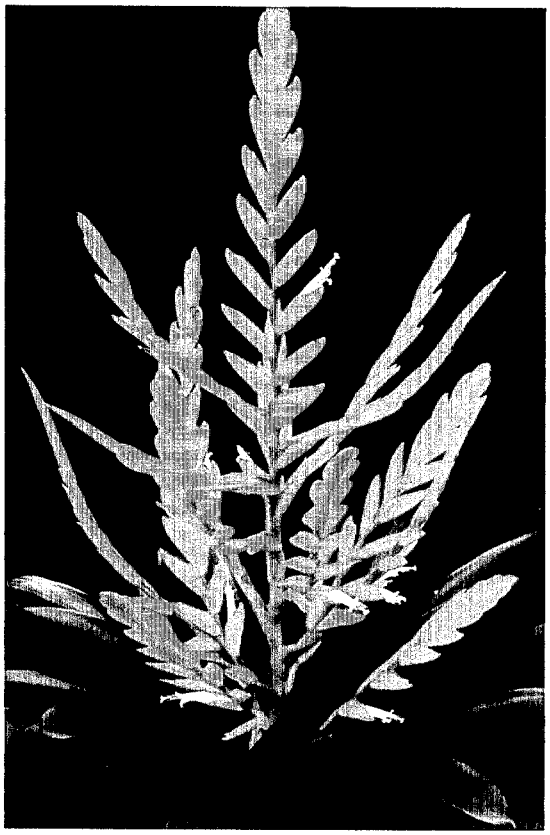

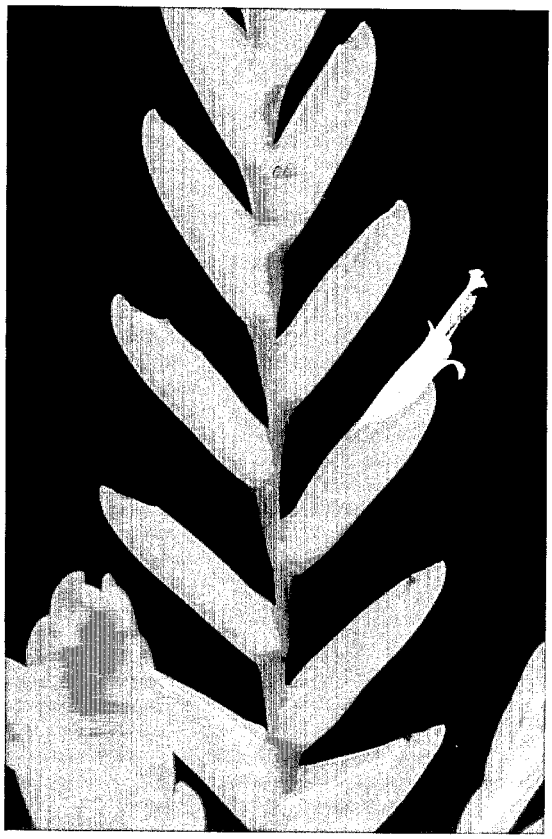

* * * * *